United States Patent [19]

Kleemann et al.

[11] Patent Number: 5,571,842
[45] Date of Patent: Nov. 5, 1996

[54] PERFLUOROALKYL-SUBSTITUTED, BENZOYLGUANIDINES, A PROCESS FOR THEIR PREPARATION, THEIR USE AS A MEDICAMENT OR DIAGNOSTIC AGENT, AND A MEDICAMENT CONTAINING THEM

[75] Inventors: Heinz-Werner Kleemann, Bischofsheim; Hans-Jochen Lang, Hofheim; Jan-Robert Schwark, Frankfurt; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 438,795

[22] Filed: May 11, 1995

[30] Foreign Application Priority Data

May 13, 1994 [DE] Germany .................. 44 17 004.1

[51] Int. Cl.$^6$ .................. A61K 31/165; C07C 323/23
[52] U.S. Cl. .................. 514/618; 514/519; 514/520; 514/521; 514/522; 558/412; 558/413; 558/414; 558/415; 564/162; 564/235
[58] Field of Search .................. 564/162, 230, 564/237; 514/618, 519, 520, 521, 522; 558/412, 413, 414, 415

[56] References Cited

U.S. PATENT DOCUMENTS

| | | | |
|---|---|---|---|
| 3,780,027 | 12/1973 | Cragoe, Jr. et al. | 260/239.6 |
| 5,091,394 | 2/1992 | Englert et al. | 514/331 |
| 5,373,024 | 12/1994 | Lang et al. | 514/618 |

FOREIGN PATENT DOCUMENTS

| | | |
|---|---|---|
| 556673 | 8/1993 | European Pat. Off. . |
| 577024 | 1/1994 | European Pat. Off. . |
| 602522 | 6/1994 | European Pat. Off. . |
| 627413 | 12/1994 | European Pat. Off. . |

Primary Examiner—Shailendra Kumar
Attorney, Agent, or Firm—Finnegan, Henderson, Farabow, Garrett & Dunner, L.L.P.

[57] ABSTRACT

Perfluoroalkyl-substituted benzoylguanidines, a process for their preparation, their use as a medicament or diagnostic agent, and a medicament containing them A description is given of perfluoroalkyl-substituted benzoylguanidines of the formula I

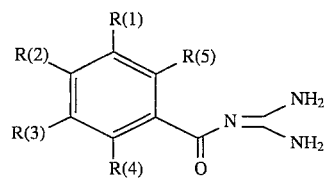

where R(1) is $(C_1-C_6)$-perfluoroalkyl-$SO_m$; R(2) and R(3) are H, halogen, alk(yl)(oxy), phenoxy; R(4) and R(5) are H, alkyl, Hal, CN, OR(7), NR(8)R(9), —$(CH_2)_n$—$(CF_2)_o$—$CF_3$ and of the pharmacologically acceptable salts thereof; the compounds I are obtained by reacting a compound II

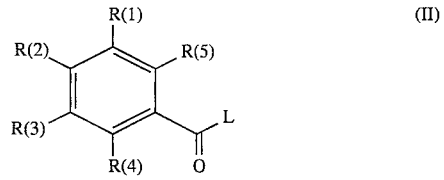

with guanidine, L being a leaving group which is able readily to undergo nucleophilic substitution.

9 Claims, No Drawings

PERFLUOROALKYL-SUBSTITUTED, BENZOYLGUANIDINES, A PROCESS FOR THEIR PREPARATION, THEIR USE AS A MEDICAMENT OR DIAGNOSTIC AGENT, AND A MEDICAMENT CONTAINING THEM

The invention relates to benzoylguanidines of the formula I

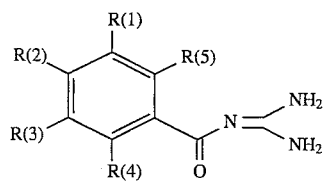

in which:
R(1) is R(6)—SO$_m$;
m is zero, 1 or 2;
R(6) is perfluoroalkyl of 1, 2, 3, 4, 5 or 6 carbon atoms which is straight-chain or branched;
R(2) and R(3) independently of one another are hydrogen, F, Cl, Br, I, alkyl of 1, 2, 3 or 4 carbon atoms, alkoxy of 1, 2, 3 or 4 carbon atoms, or phenoxy which is unsubstituted or is substituted by 1–3 substituents selected from the group consisting of F, Cl, methyl and methoxy; or
R(2) and R(3) independently of one another are 1-pyrrolyl, 2-pyrrolyl or 3-pyrrolyl which is unsubstituted or is substituted by 1 to 4 substituents selected from the group consisting of F, Cl, Br, I, CN, alkanoyl of 2, 3, 4, 5, 6, 7 or 8 carbon atoms, alkoxycarbonyl of 2, 3, 4, 5, 6, 7 or 8 carbon atoms, formyl, carboxyl, CF$_3$, methyl and methoxy;
R(4) and R(5) independently of one another are hydrogen, alkyl of 1, 2 or 3 carbon atoms, F, Cl, Br, I, CN, OR(7), NR(8)R(9), —(CH$_2$)$_n$—(CF$_2$)$_o$—CF$_3$;
R(7), R(8) and R(9) independently of one another are hydrogen or alkyl of 1, 2, 3 or 4 carbon atoms;
n is zero or 1;
o is zero, 1 or 2;
and the pharmacologically acceptable salts thereof.
Preferred compounds of the formula I are those in which:
R(1) is R(6)—SO$_m$;
m is zero, 1 or 2;
R(6) is perfluoroalkyl of 1, 2, 3 or 4 carbon atoms which is straight-chain or branched;
R(2) and R(3) independently of one another are hydrogen, F, Cl, Br, alkyl of 1, 2, 3 or 4 carbon atoms, alkoxy of 1, 2, 3 or 4 carbon atoms, or phenoxy which is unsubstituted or is substituted by 1–2 substituents selected from the group consisting of F, Cl, methyl and methoxy; or
R(2) and R(3) independently of one another are 1-pyrrolyl, 2-pyrrolyl or 3-pyrrolyl which is unsubstituted or is substituted by 1 or 2 substituents selected from the group consisting of F, Cl, Br, I, CN, alkanoyl of 2, 3, 4 or 5 carbon atoms, alkoxycarbonyl of 2, 3, 4 or 5 carbon atoms, formyl, carboxyl, CF$_3$ or methyl;
R(4) and R(5) independently of one another are hydrogen, alkyl of 1, 2 or 3 carbon atoms, F, Cl, Br, OH, NH$_2$, —(CF$_2$)$_o$—CF$_3$;
o is zero, 1 or 2;
and the pharmacologically acceptable salts thereof.
Particularly preferred compounds of the formula I are those in which:

R(1) is —SO$_2$CF$_3$;
R(2) and R(3) independently of one another are hydrogen, F, Cl, Br, alkyl of 1, 2, 3 or 4 carbon atoms, methoxy, or phenoxy which is unsubstituted or is substituted by one substituent from the group consisting of F, Cl, methyl and methoxy; or
R(2) and R(3) independently of one another are 1-pyrrolyl, 2-pyrrolyl or 3-pyrrolyl which is unsubstituted or substituted by 1 or 2 substituents selected from the group consisting of F, Cl, Br, I, CN, alkanoyl of 2, 3, 4 or 5 carbon atoms, alkoxycarbonyl of 2, 3, 4 or 5 carbon atoms, formyl, carboxyl, CF$_3$ and methyl;
R(4) and R(5) independently of one another are hydrogen, methyl, F, Cl, Br, OH, NH$_2$, —CF$_3$;
and the pharmacologically acceptable salts thereof.

Where one of the substituents R(1) to R(6) contains one or more centers of asymmetry, then the configuration thereof may be either S or R. The compounds may be in the form of optical isomers, diastereomers, racemates or mixtures thereof.

The alkyl radicals referred to may be either straight-chain or branched.

The invention further relates to a process for the preparation of the compounds I, which comprises reacting a compound of the formula II

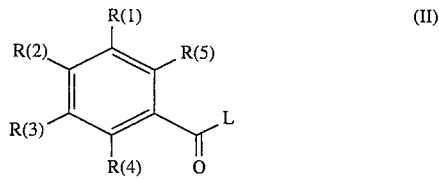

in which R(1) to R(5) are as defined and L is a leaving group which readily undergoes nucleophilic substitution, with guanidine.

The activated acid derivatives of the formula II, in which L is an alkoxy group, preferably a methoxy group, a phenoxy, phenylthio, methylthio or 2-pyridylthio group, or a nitrogen heterocycle, preferably 1-imidazolyl, are advantageously obtained in a manner known per se from the corresponding carboxylic acid chlorides (formula II, L=Cl), which in turn can be prepared in a manner known per se from the corresponding carboxylic acids (formula II, L=OH) using, for example, thionyl chloride.

In addition to the carboxylic acid chlorides of the formula II (L=Cl) it is also possible to prepare other activated acid derivatives of the formula II in a manner known per se directly from the corresponding benzoic acid derivatives (formula II, L=OH); for example, the methyl esters of the formula II where L=OCH$_3$ can be prepared by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, and also the activations of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for the preparation of activated carboxylic acid derivatives of the formula II is given, with indications of source literature, in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. In this context, for the reaction of the methyl benzoates (II, L=OMe) with guanidine, methanol, isopropanol or THF at from 20° C. to the boiling point of these solvents has proven suitable. The majority of reactions of compounds II with salt-free guanidine have been advantageously carried out in aprotic inert solvents such as THF, dimethoxyethane and dioxane. However, with the use of a base such as, for example, NaOH, water can also be used as solvent in the reaction of II with guanidine.

If L is Cl, the reaction is advantageously carried out with the addition of an acid scavenger, for example in the form of excess guanidine, in order to bind the hydrohalic acid.

Some of the corresponding benzoic acid derivatives of the formula II are known and are described in the literature. Those compounds of the formula II which are not known can be prepared by methods which are known from the literature. The benzoic acids obtained are reacted by one of the process variants described above to give compounds I according to the invention.

The introduction of some substituents in position 3, 4 and 5 is carried out by methods known from the literature for the palladium-mediated cross-coupling of aryl halides or aryl triflates with, for example, organostannanes, organoboronic acids or organoboranes, or organocopper or organozinc compounds.

The introduction of some substituents in position 4 is carried out by methods known from the literature for nucleophilic substitution in the aromatic ring system.

The synthesis of a perfluoroalkylsulfonyl group in position 3 is carried out by methods known from the literature, from the sulfonyl fluoride using a perfluoroalkyltrimethylsilane.

Benzoylguanidines I are in general weak bases and are able to bind acid with the formation of salts. Suitable acid addition salts are salts of all pharmacologically tolerated acids, for example halides, especially hydrochlorides, lactates, sulfates, citrates, tartrates, acetates, phosphates, methylsulfonates and p-toluenesulfonates.

The compounds I are substituted acylguanidines.

The most prominent representative of the acylguanidines is the pyrazine derivative amiloride, which is used in therapy as a potassium-sparing diuretic agent. Many other compounds of the amiloride type are described in the literature, examples being dimethylamiloride or ethylisopropylamiloride.

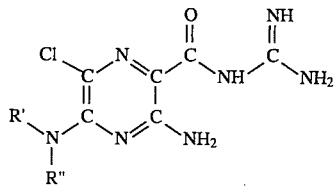

Amiloride: R' and R"=H
Dimethylamiloride: R' and R"=CH$_3$
Ethylisopropylamiloride: R'=C$_2$H$_5$ and R"=CH(CH$_3$)$_2$ In addition to this, investigations have been disclosed which point to amiloride having antiarrhythmic properties (Circulation 79, 1257–63 (1989)). However, a factor countering any widespread use of amiloride as an antiarrhythmic agent is that this effect is only weakly pronounced and is accompanied by hypotensive and saluretic effects, which latter side-effects are undesirable when treating cardiac arrhythmias.

Indications of the antiarrhythmic properties of amiloride have also been obtained in experiments on isolated animal hearts (Eur. Heart J. 9 (suppl.1): 167 (1988) (book of abstracts)). Thus it was found using rat hearts, for example, that artificially induced ventricular fibrillation could be completely suppressed by amiloride. The abovementioned amiloride derivative ethylisopropylamiloride was even more potent than amiloride in this model system.

U.S. Pat. No. A-5,091,394 (HOE 89/F 288) describes benzoylguanidines which have a hydrogen atom in the position corresponding to the radical R(1). German Patent Application P 42 04 575.4 (HOE 92/F 034) proposes benzoylguanidines but in which the substituents do not have the definitions claimed according to the present invention. This patent application corresponds to South African Patent 93-0984.

U.S. Pat. No. A-3,780,027 claims acylguanidines which are structurally similar to the compounds of the formula I and are derived from commercially available loop diuretics, such as bumetanide. Correspondingly, these compounds are reported to have a strong salidiuretic activity. It was surprising, therefore, that the compounds according to the invention do not exhibit any unwanted and disadvantageous salidiuretic properties, but do exhibit very good antiarrhythmic properties, which are important for the treatment of diseases which occur, for example, in association with symptoms of lack of oxygen. As a consequence of their pharmacological properties, the compounds are outstandingly suitable as antiarrhythmic pharmaceuticals possessing a cardioprotective component for the prophylaxis and treatment of infarction and for the treatment of angina pectoris, in which context they also inhibit or sharply reduce, in a preventive manner, the pathophysiological processes associated with the development of ischemically induced damage, especially in the case of the initiation of ischemically induced cardiac arrhythmias. Owing to their protective effects against pathological hypoxic and ischemic situations, the compounds of the formula I according to the invention can, as a consequence of inhibiting the cellular Na$^{30}$/H$^+$ exchange mechanism, be used as pharmaceuticals for the treatment of all acute or chronic damage induced by ischemia, or diseases induced primarily or secondarily thereby. This relates to their use as pharmaceuticals for surgical interventions, for example in organ transplants, where the compounds can be used both for protecting the organs in the donor prior to and during removal, for protecting organs which have been removed, for example when they are being treated with or stored in physiological bath fluids, and when transferring the organs into the recipient. The compounds are likewise valuable protective pharmaceuticals when angioplastic surgical interventions are carried out, for example on the heart and also on peripheral vessels. In accordance with their protective effect against ischemically induced damage, the compounds are also suitable as pharmaceuticals for the treatment of ischemias of the nervous system, in particular of the central nervous system, in which context they are suitable, for example, for treating stroke or cerebral edema. Over and above this, the compounds of the formula I according to the invention are also suitable for treating forms of shock, for example allergic, cardiogenic, hypovolemic and bacterial shock.

In addition, the compounds of the formula I according to the invention are notable for their strong inhibitory effect on the proliferation of cells, for example the proliferation of fibroblast cells and the proliferation of the smooth vascular muscle cells. For this reason, the compounds of the formula I are valuable therapeutic agents for diseases in which cell proliferation represents a primary or secondary cause, and may therefore be used as antiatherosclerotic agents, and as agents against diabetic late complications, cancerous diseases, fibrotic diseases such as pulmonary fibrosis, hepatic fibrosis or renal fibrosis, and against organ hypertrophies and hyperplasias, in particular against hyperplasia or hypertrophy of the prostate.

The compounds according to the invention are highly effective inhibitors of the cellular sodium/proton antiporter ($Na^{3O}/H^+$ exchanger) which, in numerous diseases (essential hypertension, atherosclerosis, diabetes, etc.), is also elevated in those cells which are readily accessible to measurement, for example in erythrocytes, thrombocytes or leucocytes. The compounds according to the invention are therefore suitable as outstanding and simple scientific tools, for example in their use as diagnostic agents for determining and differentiating particular forms of hypertension, but also of atherosclerosis, diabetes, proliferative diseases, etc. In addition to this, the compounds of the formula I are suitable for preventive therapy for preventing the genesis of high blood pressure, for example of essential hypertension.

In this context, pharmaceuticals which comprise a compound I may be administered orally, parenterally, intravenously or rectally, or by inhalation, the preferred route of administration depending on the particular features of the disease. In this case the compounds I may be used alone or together with pharmaceutical auxiliary substances, both in veterinary and in human medicine.

The auxiliary substances which are suitable for the desired pharmaceutical formulation are familiar to the person skilled in the art on the basis of his or her specialist knowledge. In addition to solvents, gel formers, suppository bases, tablet auxiliaries and other active-compound excipients it is possible, for example, to employ antioxidants, dispersants, emulsifiers, defoamers, taste corrigents, preservatives, solubilizers or dyes.

For a form for oral administration, the active compounds are mixed with the additives which are suitable for the purpose, such as excipients, stabilizers or inert diluents, and the mixture is brought by the customary methods into the appropriate administration forms, such as tablets, coated tablets, hard gelatin capsules or aqueous, alcoholic or oily solutions. Examples of inert excipients which may be used are gum arabic, magnesium hydroxide, magnesium carbonate, potassium phosphate, lactose, glucose or starch, especially corn starch. In this context, the preparation can be effected either as dry granules or as wet granules. Examples of suitable oily excipients or solvents are vegetable or animal oils, such as sunflower oil or cod-liver oil.

For subcutaneous or intravenous administration, the active compounds are brought into solution, suspension or emulsion with, if desired, the substances which are conventional for this purpose, such as solubilizers, emulsifiers or other auxiliaries. Examples of suitable solvents are water, physiological sodium chloride solution or alcohols, for example ethanol, propanol or glycerol, and also sugar solutions, such as solutions of glucose or mannitol, or else a mixture of the various solvents mentioned.

Examples of pharmaceutical formulations which are suitable for administration in the form of aerosols or sprays are solutions, suspensions or emulsions of the active compound of the formula I in a pharmaceutically unobjectionable solvent, such as, in particular, ethanol or water, or in a mixture of such solvents.

The formulation can as required also contain additional pharmaceutical auxiliaries, such as surfactants, emulsifiers and stabilizers, and also a propellant gas. Such a preparation customarily comprises the active compound in a concentration of from about 0.1 to 10% by weight, in particular from about 0.3 to 3% by weight.

The dosage of the active compound of the formula I to be administered, and the frequency of administration, depend on the strength and duration of the effect of the compounds used, and also on the nature and severity of the disease to be treated and on the sex, age, weight and individual responsiveness of the mammal to be treated. On average, the daily dose of a compound of the formula I for a patient weighing about 75 kg is at least 0.001 mg/kg, preferably 0.01 mg/kg, up to at most 10 mg/kg, preferably 1 mg/kg of body weight. In acute manifestations of the disease, for instance immediately after suffering a cardiac infarction, even higher and, in particular, more frequent dosages may be necessary, for example up to 4 individual doses per day. In the case of i.v. administration, in particular, for instance in an infarction patient in intensive care, up to 200 mg per day may be necessary.

List of abbreviations:

| | |
|---|---|
| MeOH | methanol |
| DMF | N,N-dimethylformamide |
| NBS | N-bromosuccinimide |
| AIBN | $\alpha,\alpha$-azobisisobutyronitrile |
| EI | electron impact |
| DCI | desorption chemical ionization |
| RT | room temperature |
| EA | ethyl acetate (EtOAc) |
| DIP | diisopropyl ether |
| MTB | methyl tert-butyl ether |
| m.p. | melting point |
| HEP | n-heptane |
| DME | dimethoxyethane |
| FAB | fast atom bombardment |
| $CH_2Cl_2$ | dichloromethane |
| THF | tetrahydrofuran |
| eq | equivalent |
| ES | electrospray ionization |

Experimental Section

General Procedure for the Preparation of Benzoylguanidines (I)

Variant A: from benzoic acids (II, L=OH) 0.01 mol of the benzoic acid derivative of the formula II is dissolved or suspended in 60 ml of anhydrous THF, and then 1.78 g (0,011 mol) of carbonyldiimidazole are added. The reaction solution is stirred over 2 hours at RT and then 2.95 g (0.05 mol) of guanidine are introduced. The mixture is stirred overnight and then the THF is distilled off under reduced pressure (rotary evaporator), water is added, the pH is adjusted to 6 to 7 with 2N HCl, and the corresponding benzoylguanidine (formula I) is filtered off. The benzoylguanidines obtained in this way can be converted into the corresponding salts by treatment with aqueous, methanolic or ethereal hydrochloric acid or other pharmacologically tolerated acids.

General Procedure for the Preparation of Benzoylguanidines (I)

Variant B: from alkyl benzoates (II, L=0-alkyl) 5 mmol of the alkyl benzoate of the formula II and 25 mmol of guanidine (free base) are dissolved in 15 ml of isopropanol or suspended in 15 ml of THF and are boiled under reflux until conversion is complete (monitoring by thin-layer chromatography; typical reaction time from 2 to 5 h). The solvent is distilled off under reduced pressure (rotary evaporator) and the residue is taken up in 300 ml of EA and washed with 3×50 ml of NaHCO$_3$ solution. Drying takes place over Na$_2$SO$_4$, the solvent is distilled off in vacuo and the residue is chromatographed on silica gel using a suitable eluent, for example EA/MeOH 5:1. (Salt formation: compare Variant A)

EXAMPLE 1

4-(4-Fluorophenoxy)-3-trifluoromethylsulfonylbenzoylguanidine

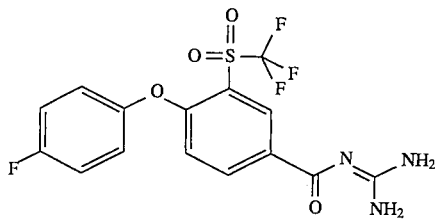

a) 2-Bromo-5-methylbenzenesulfonic acid 140 g of 2-amino-5-methylbenzenesulfonic acid are dissolved in 810 g of 30% aqueous HBr solution, and a solution of 51.8 g of NaNO$_2$ in 100 ml of water is added dropwise at 0°–5° C. The mixture is subsequently stirred at 0° C. for 10 min and then the diazonium salt is poured into a solution of 143.5 g of CuBr in 250 ml of half-concentrated aqueous HBr solution. The mixture is then carefully heated over a steam bath (about 40°–50° C.) until the evolution of nitrogen has ended. A little active charcoal is added and is filtered off while the mixture is hot. The mixture is then diluted with water and the solid is filtered off. The filtrate is saturated with NaCl in the course of which the desired product precipitates out in the form of colorless crystals and is filtered off.

m.p.>250° C.

R$_f$ (EA/MeOH 3:1)=0.23 MS (DCI): 252 (M+H)$^+$ b) 2-Bromo-5-methylbenzenesulfonyl chloride 50 g of 2-bromo-5-methylbenzenesulfonic acid and 41.5 g of PCl$_5$ are carefully heated in 500 ml of toluene until the evolution of gas commences. After the reaction has subsided the mixture is boiled under reflux until the evolution of gas has ended (2 h). The mixture is cooled and the toluene and POCl$_3$ are removed in vacuo. The residue is carefully poured onto about 1 l of ice, the mixture is subsequently stirred for 1 h and then the product is filtered off with suction. Drying at 60° C. in vacuo gives 36 g of a colorless solid.

MS (DCI): 269 (M+H)$^+$ c) 2-Bromo-5-methylbenzenesulfonyl fluoride 32 g of 2-bromo-5-methylbenzenesulfonyl chloride are dissolved in 75 ml of dioxane, and a solution of 20.6 g of KF in 20 ml of water is added. The mixture is stirred at 45° C. for 48 h, poured into 500 ml of water and stirred subsequently for 30 min, and finally the product is filtered off with suction. 24 g of a colorless solid.

MS (DCI): 253 (M+H)$^+$ d) 2-Bromo-5-methylphenyl trifluoromethyl sulfone 21.4 g of 2-bromo-5-methylbenzenesulfonyl fluoride are dissolved in 225 ml of a 0.5M solution of Me$_3$SiCF$_3$ in THF. A solution of 2.5 g of tris(dimethylamino)-sulfur(trimethylsilyl) difluoride in 100 ml of THF is then slowly added dropwise at 25°–30° C. The mixture is stirred at RT for 3 h, 200 ml of saturated aqueous NaCl solution are added, and the mixture is extracted with 3×300 ml of EA. The combined organic phases are dried over Na$_2$SO$_4$ and the solvent is removed in vacuo. The crude product is chromatographed once with EA/HEP 1:4 and a second time with MTB. 13 g of colorless crystals are obtained, m.p. 69° C.

R$_f$ (EA/HEP 1:4)=0.30 MS (DCI): 303 (M+H)$^+$ e) 2-Bromo-5-tribromomethylphenyl trifluoromethyl sulfone 1 g of 2-bromo-5-methylphenyl trifluoromethyl sulfone, 350 µl of bromine and a catalytic amount (about 50 mg) of benzoyl peroxide are stirred in 30 ml of chlorobenzene at 130° C. for 8 h under irradiation with a 300 W incandescent lamp. A further catalytic amount of benzoyl peroxide is added hourly. A further 300 µl of bromine are added and the mixture is stirred at 130° C. for 14 h more. The reaction mixture is cooled and decolorized with excess aqueous Na$_2$SO$_3$ solution, 100 ml of saturated aqueous NaCl solution are added, and the mixture is extracted with 3×100 ml of EA. The combined organic phases are dried over Na$_2$SO$_4$ and the solvent is removed in vacuo. Chromatography with EA/HEP 1:4 gives 1.1 g of a colorless oil.

R$_f$ (EA/HEP 1:4)=0.43 MS (DCI): 537 (M+H)$^+$ f) Methyl 4-bromo-3-trifluoromethylsulfonylbenzoate 250 mg of 2-bromo-5-tribromomethylphenyl trifluoromethyl sulfone are dissolved in 3 ml of MeOH, and a solution of 236 mg of AgNO$_3$ in 5 ml of water is added. The mixture is stirred at RT for 30 min, the precipitate is filtered off, excess aqueous HCl solution is added to the filtrate, and solids are again filtered off. The filtrate is concentrated in vacuo to give 190 mg of a pale yellow oil.

R$_f$ (DIP)=0.59 MS (DCI): 347 (M+H)$^+$ g) Methyl 4-(4-fluorophenoxy)-3-trifluoromethylsulfonylbenzoate 500 mg of methyl 4-bromo-3-trifluoromethylsulfonylbenzoate, 162 mg of 4-fluorophenol and 600 mg of K$_2$CO$_3$ are stirred in 10 ml of DMF at 120° C. for 1.5 h. 100 ml of water are then added and the mixture is extracted with 3×100 ml of EA. The combined organic phases are dried over Na$_2$SO$_4$ and the solvent is removed in vacuo. Chromatography with DIP gives 278 mg of a colorless oil.

R$_f$ (EA/HEP 1:4)=0.17 MS (DCI): 379 (M+H)$^+$ h) 4-(4-Fluorophenoxy)-3-trifluoromethylsulfonylbenzoylguanidine 260 mg of methyl 4-(4-fluorophenoxy)-3-trifluoromethylsulfonylbenzoate are reacted in accordance with Variant B to give 53 mg of product; m.p. (hydrochloride) 160° C. (decomposition).

R$_f$ (EA)=0.32 MS (DCI):406 (M+H)$^+$

EXAMPLE 2

4-Isopropyl-3-trifluoromethylsulfonylbenzoylguanidine

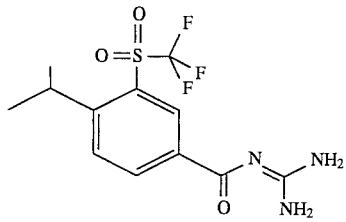

a) 2-Isopropylbenzenesulfonyl chloride 20 g of 2-isopropylthiophenol are emulsified in 500 ml of water. Chlorine is passed in up to saturation at about 10° C., and the mixture is subsequently stirred at 10°–20° C. for 30 min. Excess chlorine is blown off with nitrogen, and the mixture is extracted with 3×200 ml of EA. The combined organic phases are dried over $Na_2SO_4$ and the solvent is removed in vacuo. 27.0 g of a colorless oil are obtained.

MS (DCl): 219 $(M+H)^+$ b) 2-Isopropylbenzenesulfonyl fluoride 27 g of 2-isopropylbenzenesulfonyl chloride and 22 g of KF are stirred in 75 ml of dioxane and 20 ml of water at 45° C. for 27 h and at RT for 45 h. 800 ml of water are then added, and the mixture is extracted with 3×300 ml of EA. The combined organic phases are dried over $Na_2SO_4$ and the solvent is removed in vacuo. 24 g of a colorless oil are obtained.

MS (DCl): 203 $(M+H)^+$ c) 2-Isopropylphenyl trifluoromethyl sulfone 17.4 g of 2-isopropylbenzenesulfonyl fluoride are dissolved in 230 ml of a 0.5M solution of $Me_3SiCF_3$ in THF. 2.7 g of tris(dimethylamino)-sulfur-(trimethylsilyl) difluoride are then added in portions at 20°–30° C. The mixture is stirred at RT for 2 h and then the solvent is removed in vacuo. The residue is taken up in 500 ml of EA and the mixture is washed with 2×150 ml of saturated aqueous NaCl solution. The combined organic phases are dried over $Na_2SO_4$ and the solvent is removed in vacuo. 19.8 g of a colorless oil are obtained.

$R_f$ (EA/HEP 1:4)=0.20 MS (DCl): 253 $(M+H)^+$ d) 2-Isopropyl-5-iodophenyl trifluoromethyl sulfone 2.52 g of 2-isopropylphenyl trifluoromethyl sulfone are dissolved in 10 ml of trifluoromethanesulfonic acid, and 2.55 g of N-iodosuccinimide are added at 0° C. The mixture is stirred at RT for 3 h, then poured into 100 ml of water and extracted with 3×100 ml of diethyl ether. The organic phase is then washed in succession with 100 ml of saturated aqueous $Na_2CO_3$ solution, 100 ml of saturated aqueous $Na_2SO_3$ solution and again with 100 ml of saturated aqueous $Na_2CO_3$ solution. The organic phase is dried over $Na_2SO_4$, the solvent is removed in vacuo and the residue is chromatographed with EA/HEP 1:8. 2.2 g of a colorless oil are obtained.

$R_f$ (EA/HEP 1:8)=0.46 MS (DCl): 379 $(M+H)^+$ e) Methyl 4-isopropyl-3-trifluoromethylsulfonylbenzoate 1.2 g of 2-isopropyl-5-iodophenyl trifluoromethyl sulfone, 1.5 ml of tri-n-butylamine, 16 mg of Pd(II) acetate and 27 mg of 1,3-bis(diphenylphosphine)propane are dissolved in 3 ml of n-butanol and 6 ml of DMF and the solution is stirred under CO gas at 100° C. for 5 h. The solvents are removed in vacuo, the residue is taken up in 100 ml of EA, and this mixture is then washed with 100 ml of saturated aqueous $Na_2CO_3$ solution and then with 100 ml of saturated aqueous $NaHSO_4$ solution. The organic phase is dried over $Na_2SO_4$ and the solvent is removed in vacuo. Chromatography of the residue with EA/HEP 1:8 gives 560 mg of a colorless oil.

$R_f$ (EA/HEP 1:8)=0.32 MS (DCl): 353 $(M+H)^+$ f) 4-Isopropyl-3-trifluoromethylsulfonylbenzoylguanidine 560 mg of methyl 4-isopropyl-3-trifluoromethylsulfonylbenzoate are converted in accordance with Variant B into 140 mg of a colorless crystalline product.

m.p. (hydrochloride) 192° C.

$R_f$ (EA)=0.44 MS (DCl): 338 $(M+H)^+$

Pharmacological Data

Inhibition of the $Na^{30}/H^+$ Exchanger of Rabbit Erythrocytes

White New Zealand rabbits (Ivanovas) received a standard diet containing 2% cholesterol for six weeks, in order to activate $Na^+/H^+$ exchange and thus to enable the $Na^+$ influx into the erythrocytes via $Na^{30}/H^+$ exchange to be determined by flame photometry. The blood was taken from the auricular arteries and made incoagulable by means of 25 IU of potassium heparin. A portion of each sample was used for duplicate determination of the hematocrit by centrifugation. Aliquots of in each case 100 μl were used to measure the initial $Na^+$ content of the erythrocytes.

In order to determine the amiloride-sensitive sodium influx, 100 μl of each blood sample were incubated at 37° C. and at pH 7.4 in each case in 5 ml of a hyperosmolar salt-sucrose medium (in mmol/l: 140 NaCl, 3 KCl, 150 sucrose, 0.1 ouabain, 20 trishydroxymethylaminomethane). The erythrocytes were then washed three times with ice-cold $MgCl_2$-ouabain solution (in mmol/l: 112 $MgCl_2$, 0.1 ouabain) and hemolyzed in 2.0 ml of distilled water. The intracellular sodium content was determined by flame photometry.

The net $Na^+$ influx was calculated from the difference between the initial sodium values and the sodium content of the erythrocytes after incubation. The amiloride-inhibitable sodium influx was given by the difference of the sodium content of the erythrocytes after incubation with and without $3\times10^{-4}$ mol/l of amiloride. This procedure was repeated with the compounds according to the invention.

Results

| Inhibition of the Na$^+$/H$^+$ exchanger: | |
|---|---|
| Example | IC$_{50}$ (μmol/l) |
| 1 | 0.2 |
| 2 | 0.07 |

We claim:

1. A benzoylguanidine of the formula I

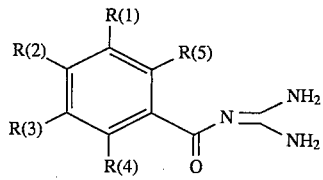

in which:
R(1) is R(6)—SO$_m$;
m is zero, 1 or 2;
R(6) is perfluoroalkyl of 1, 2, 3, 4, 5 or 6 carbon atoms which is straight-chain or branched;
R(2) and R(3) independently of one another are hydrogen, F, Cl, Br, I, alkyl of 1, 2, 3 or 4 carbon atoms, alkoxy of 1, 2, 3 or 4 carbon atoms, or phenoxy which is unsubstituted or is substituted by 1–3 substituents selected from the group consisting of F, Cl, methyl and methoxy;
R(4) and R(5) independently of one another are hydrogen, alkyl of 1, 2 or 3 carbon atoms, F, Cl, Br, I, CN, OR(7), NR(8)R(9), —(CH$_2$)$_n$—(CF$_2$)$_o$—CF$_3$;
R(7), R(8) and R(9) independently of one another are hydrogen or alkyl of 1, 2, 3 or 4 carbon atoms;
n is zero or 1;
o is zero, 1 or 2;
or a pharmacologically acceptable salt thereof.

2. A compound of the formula I as claimed in claim 1, in which:
R(1) is R(6)—SO$_m$;
m is zero, 1 or 2;
R(6) is perfluoroalkyl of 1, 2, 3 or 4 carbon atoms which is straight-chain or branched;
R(2) and R(3) independently of one another are hydrogen, F, Cl, Br, alkyl of 1, 2, 3 or 4 carbon atoms, alkoxy of 1, 2, 3 or 4 carbon atoms, or phenoxy which is unsubstituted or is substituted by 1–2 substituents selected from the group consisting of F, Cl, methyl and methoxy;
R(4) and R(5) independently of one another are hydrogen, alkyl of 1, 2 or 3 carbon atoms, F, Cl, Br, OH, NH$_2$, —(CF$_2$)$_o$—CF$_3$;
o is zero, 1 or 2.

3. A compound of the formula I as claimed in claim 1 in which:
R(1) is —SO$_2$CF$_3$;
R(2) and R(3) independently of one another are hydrogen, F, Cl, Br, alkyl of 1, 2, 3 or 4 carbon atoms, methoxy, or phenoxy which is unsubstituted or is substituted by one substituent from the group consisting of F, Cl, methyl and methoxy;
R(4) and R(5) independently of one another are hydrogen, methyl, F, Cl, Br, OH, NH$_2$, —CF$_3$.

4. A method for the treatment of arrhythmias which comprises administering to a host in need of said treatment an effective amount of a compound of the formula I as claimed in claim 1.

5. A pharmaceutical composition for the treatment of arrhythmias which comprises a compound of formula I as claimed in claim 1 together with a pharmaceutically acceptable carrier.

6. A method for the treatment or prophylaxis of ischemic heart conditions which comprises administering to a host in need thereof an effective amount of a compound of formula I as claimed in claim 1.

7. A pharmaceutical composition for use in surgical interventions and organ transplants which comprises a compound of formula I as claimed in claim 1 and a pharmaceutically acceptable carrier.

8. A diagnostic agent for the inhibition of the Na$^{30}$/H$^+$ exchanger and the diagnosis of hypertension and proliferative diseases which comprises a compound of formula I as claimed in claim 1.

9. A pharmaceutical composition for the treatment of cardiac infarct, angina pectoris, ischemic heart conditions, ischemic conditions of the peripheral and central nervous systems, of stroke and of the peripheral organs and limbs, and of states of shock which comprises a compound of formula I as claimed in claim 1 together with a pharmaceutically acceptable carrier.

* * * * *

UNITED STATES PATENT AND TRADEMARK OFFICE
CERTIFICATE OF CORRECTION

PATENT NO. : 5,571,842
DATED : November 05, 1996
INVENTOR(S) : Heinz-Werner KLEEMANN et al.

It is certified that error appears in the above-indentified patent and that said Letters Patent is hereby corrected as shown below:

Claim 8, Column 12, Line 35, "$Na^{30}/H^+$ should read --$Na^+H^+$--.

Signed and Sealed this

Ninth Day of September, 1997

*Attest:*

BRUCE LEHMAN

*Attesting Officer*      Commissioner of Patents and Trademarks